United States Patent [19]

Gangadharam

[11] Patent Number: 4,963,565

[45] Date of Patent: Oct. 16, 1990

[54] IN VIVO TREATMENT OF MYCOBACTERIAL INFECTIONS WITH 6-CYCLO OCTYLAMINO-5,8-QUINOLINE QUINONE

[75] Inventor: Pattisapu R. J. Gangadharam, Denver, Colo.

[73] Assignee: National Jewish Center for Immunology and Respiratory Medicine, Denver, Colo.

[21] Appl. No.: 890,720

[22] Filed: Jul. 30, 1986

[51] Int. Cl.5 ............................................. A61K 31/47
[52] U.S. Cl. ..................................................... 514/311
[58] Field of Search .......................................... 514/311

[56] References Cited

U.S. PATENT DOCUMENTS 4,492,704  1/1985  Fleisch et al. .................... 514/311

OTHER PUBLICATIONS

Chemical Abstracts 76:108223h (1972).
Chemical Abstracts 89:209669g (1978).
Tubercle 62 (1981) 37–41.
Gangadharam, et al., Am. Rev. Resp. Dis. 118: 467–473 (1978).

Primary Examiner—Jerome D. Goldberg
Attorney, Agent, or Firm—Felfe & Lynch

[57] ABSTRACT 6-cyclo-octylamino-5,8-quinoline quinone, a Vitamin K analogue, shows surprising efficacy as an in vivo therapeutic agent for treatment of tuberculosis and leprosy. Mycobacteria species, intracellulare, tuberculosis, and leprae are inhibited following administration of the compound in any form.

12 Claims, 10 Drawing Sheets

IN VIVO TREATMENT OF MYCOBACTERIAL INFECTIONS WITH 6-CYCLO OCTYLAMINO-5,8-QUINOLINE QUINONE

FIELD OF THE INVENTION

This invention relates to the field of treatment of bacterial infections, and diseases caused thereby. Specifically, mycobacterial infections caused by *Mycobacterium tuberculosis* and related organisms are treated.

BACKGROUND AND PRIOR ART

Various diseases are caused by infections by foreign bacteria. An exhaustive list of such diseases and their causative agents is not possible, but one such example is tuberculosis, caused by *Mycobacterium tuberculosis*. *Mycobacterium intracellulare* is another pathogen causing disease in humans, more so in immune compromised individuals and those with Acquired Immune Deficiency Syndrome (AIDS). Current research in the field has focused on compounds which are bactericidal and non-toxic to treat diseases caused by these organisms. Of special significance is the fact that at present no specific drugs are available to treat disease caused by *M. intracellulare* group of organisms.

The rifamycin family of antibiotics has received particular attention in this regard. For example, U.S. Pat. No. 4,086,344, discloses N,15-Didehydro-15-deoxo-3,15-epi (methano alkyl amino) rifamycins, in quinone or hydroquinone form. These compounds are only used in in vitro tests, however. While results which show biocidal activity in vitro can be applied for the development of, e.g., cleaning solutions, disinfectants, and so forth; in vitro efficacy is no guarantee that the subject compound will work in vivo.

U.S. Pat. No. 3,084,165 is indicative of this. This patent discloses quinone derivatives which are described as "tuberculostatic". Data are limited to in vitro situations, although the patent clearly shows that in vivo results in other areas were encouraging (e.g., suppression of aerobic glycolysis in tumor cells).

U.S. Pat. No. 4,327,096, also teaches compounds which are effective against tuberculosis in vitro. This patent teaches 3-amindino rifamycins which inhibits *M. tuberculosis*. This effect is also shown by U.S. Pat. No. 4,447,432, directed to azino rifamycin compounds. Additional compounds effective against tuberculosis in vitro include U.S. Pat. No. 3,691,168 (5-arylbenzo (B) (1,7) napthydrine derivatives).

In vivo success has been more limited. U.S. Pat. No. 3,995,044, discloses benzoic acid anide derivates useful against *M. tuberculosis* in vivo. Of particular interest according to this patent is N-(pyrid-2-yl-methyl) 3,5-dinitrobenzoic acid. This patent, filed in 1974, states that fourteen effective medicaments were known at that time. One such example, though not stated in the '044 patent, is the 2-substituted naphthiazole 4,9-quinones, and their hydroquinone and acyl derivatives, as disclosed in U.S. Pat. No. 3,039,925. This patent admits that, alone, these quinones are not as effective as standard anti-tuberculosis agents, (as an example, isonicotinic acid hydrazide is given); but, suggests combination with this semicarbazones of aromatic or heterocyclic aldehydes, streptomycin and paraaminosalicylic acid are effective.

The most recent patent teaching anti-tuberculosis compound is U.S. Pat. No. 4,499,075. This patent teaches polypeptide antibiotics derived from *S. coeruleorubidus* rubidus. These polypeptides are effective in vivo.

Review of this art shows that no compounds are disclosed which are effective against *M. intracellulare*, which is an important and difficult mycobacterial disease. Additionally, as is pointed out in U.S. Pat. No. 3,995,044, the need for additional drugs effective against *M. tuberculosis* continues, because of the development of resistant strains. Even with fourteen effective drugs, the '044 patent points out that combinations of three, and as many as five different drugs have been used in combination. Concerns about combinations of so many active compounds need not be repeated. The recognition, as in the '044 patent, e.g., that up to 30% of patients show side effects of anti-tuberculosis drugs, emphasizes the need for continued research in this area.

Recent research has pointed to the possible use of Vitamin K and coenzyme Q analogous as an antimycobacterial agent. Of particular interest is 6-cyclo-ocylamino-5,8,quinoline quinone (CQQ, or "Gangamicin" hereafter), a quinone derivative of Vitamin K, having the structure:

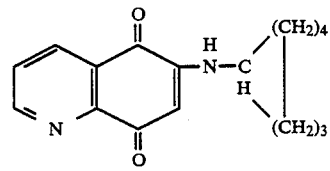

and the empirical formula $C_{17}H_{20}N_2O_2$. See, Gangadharam, et al., *Am. Rev. Respir. Disease* (1978). Vitamin K. as is shown in the art, is important in connection with blood clotting.

As CQQ is a quinone derivative, the possibility that it might be useful as an antitubercular drug arises. Several factors speak against it. First, as will be seen by review of the art, supra, the usefulness of one derivative is no guarantee of the usefulness of a second one. Second, as will also be realized from the art, in vitro efficacy does not guarantee, or even suggest, success in vivo. In connection with this is the not unwarranted concern over the similarity of CQQ to Vitamin K. As Vitamin K deficiency has been associated with excessive bleeding, CQQ could be expected to cause massive hemmorhaging in vivo.

Thus, while Gangadharam, et al., supra, and in Tubercle 62: 37 –41 (1981) have demonstrated that CQQ is effective against *M. intracellulare* and *M. tuberculosis* in vitro, it was not to be assumed that the compound would be efficacious in vivo. Now, however, it has been discovered that CQQ is effective against mycobacterial infection in vivo, especially against *M. tuberculosis* and *M. intracellulare*.

Hence it is an object of this invention to provide a method of in vivo treatment of mycobacterial infections, including *M. tuberculosis* and *M. intracellulare*, using the compound CQQ, also known as Gangamicin.

However these and other objects of the invention are achieved will be ascertained by review of the Detailed Description of Preferred Embodiments, which follows.

DETAILED DESCRIPTION OF PREFERRED EMBODIMENTS

Various in vivo and in vitro experiments were performed to determine the efficacy of CQQ against different pathological bacteria.

IN VIVO STUDIES

Animal studies were performed using the mouse model. Mice are accepted as excellent experimental models for human mycobacterial diseases. While earlier literature (see review by Youmans etc.), have established C57Bl/6 mice models for in vivo studies with *M. tuberculosis*, mouse models for experimental *M. intracellulare* infections were difficult until recently (see review by Gangadharam). The Beige mouse (C57Bl/6/bg/bg) model established by Gangadharam et al is now used for studies with *M. intracellulare*. In the in vivo studies described below, C57Bl/6 and Beige mice models are used for *M. tuberculosis* and *M. intracellulare* infections, respectively.

In chemotherapy studies, various concentrations of CQQ and ansamycin (LM 427), were used. Lung and spleen tissue samples from the animal models were used. "CFU" refers to the "colony forming units" observed when culturing these samples.

In all of the following experiments, spleens and lungs were removed aseptically from the subject animals, at different periods of challenge. The organs were ground and samples of the ground organs were plated in aliquots on 7H11 agar medium. If the bacteria were present, they would grow, forming CFUs. The plates were incubated at 37° C. (with 5% $CO_2$ for *M. tuberculosis*), and read after three weeks incubation.

CFUs were counted by visual enumeration. If increased magnification was necessary, this was done using a plate microscope.

The art recognizes that the technique detailed supra is reproducible, i.e., if a 10-fold dilution of seed inoculum is performed, normally CFU copunts will exhibit 10-fold reduction.

EXAMPLE 1
IN VIVO CHEMOTHERAPUETIC ACTIVITY OF GANGAMICIN AGAINST MYCOBACTERIUM INTRACELLULARE STUDIED IN THE ACUTE MODEL USING BEIGE MICE

Figure 1:
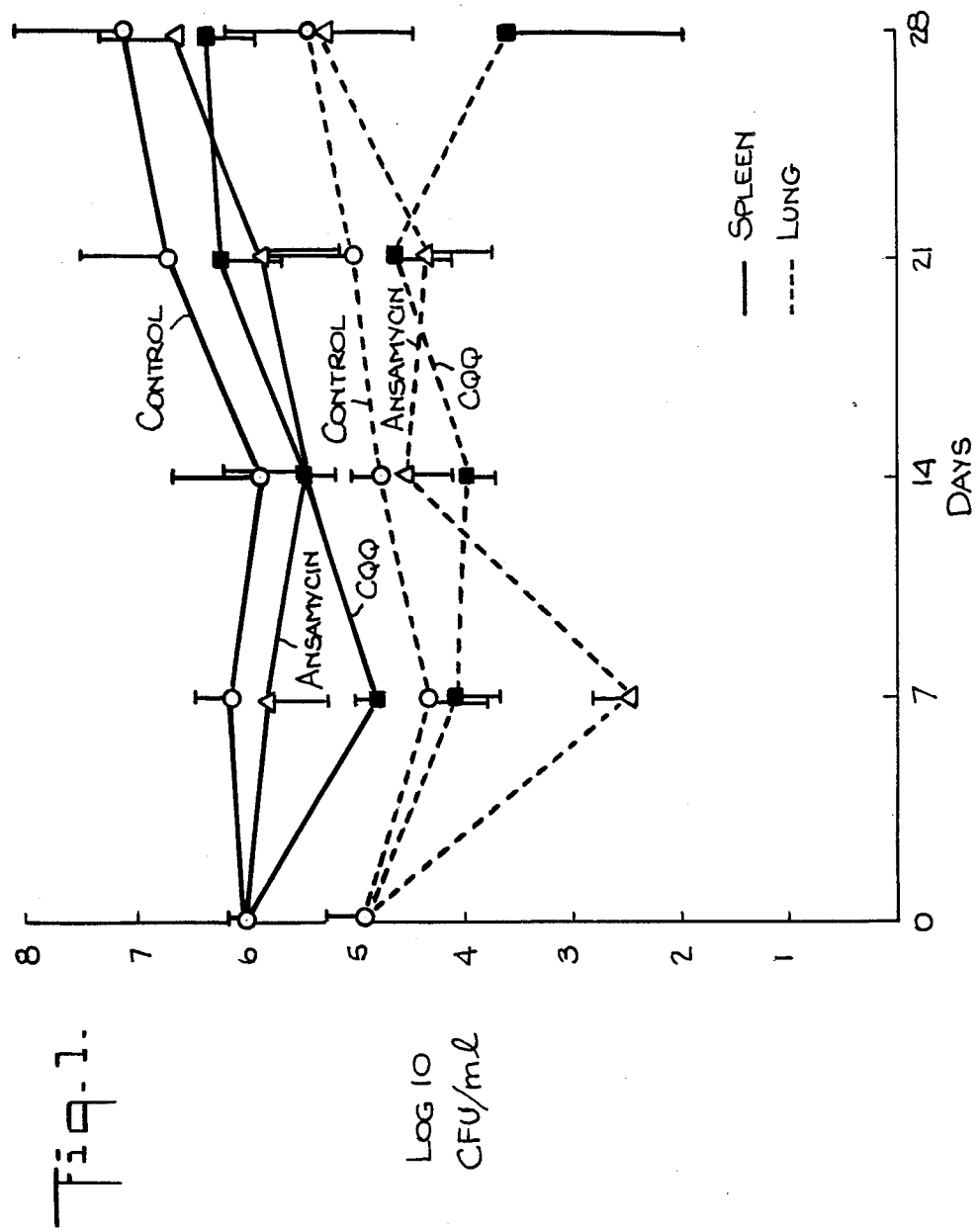

Experiments were performed using an acute model using Beige mice challenged with *M. intracellulare* strain 571-8 as described earlier. Three groups of infected Beige mice were followed: one treated with CQQ (10 mg/kg) orally daily, other with ansamycin (10 mg/kg) daily orally and the third severed as the infected untreated control. Ansamycin was chosen for comparison because it is the most active, presently available drug against *M. tuberculosis* and *M. intracellulare*. CQQ under these conditions showed considerable activity with a statistically significant difference (P 0.05) at each time point. Its activity is better than that of ansamycin (FIG. 1).

EXAMPLE II
IN VIVO CHEMOTHERAPEUTIC ACTIVITY OF GANGAMICIN AGAINST M. INTRACELLULARE STUDIED IN THE BIEGE MOUSE MODEL

Figure 2:
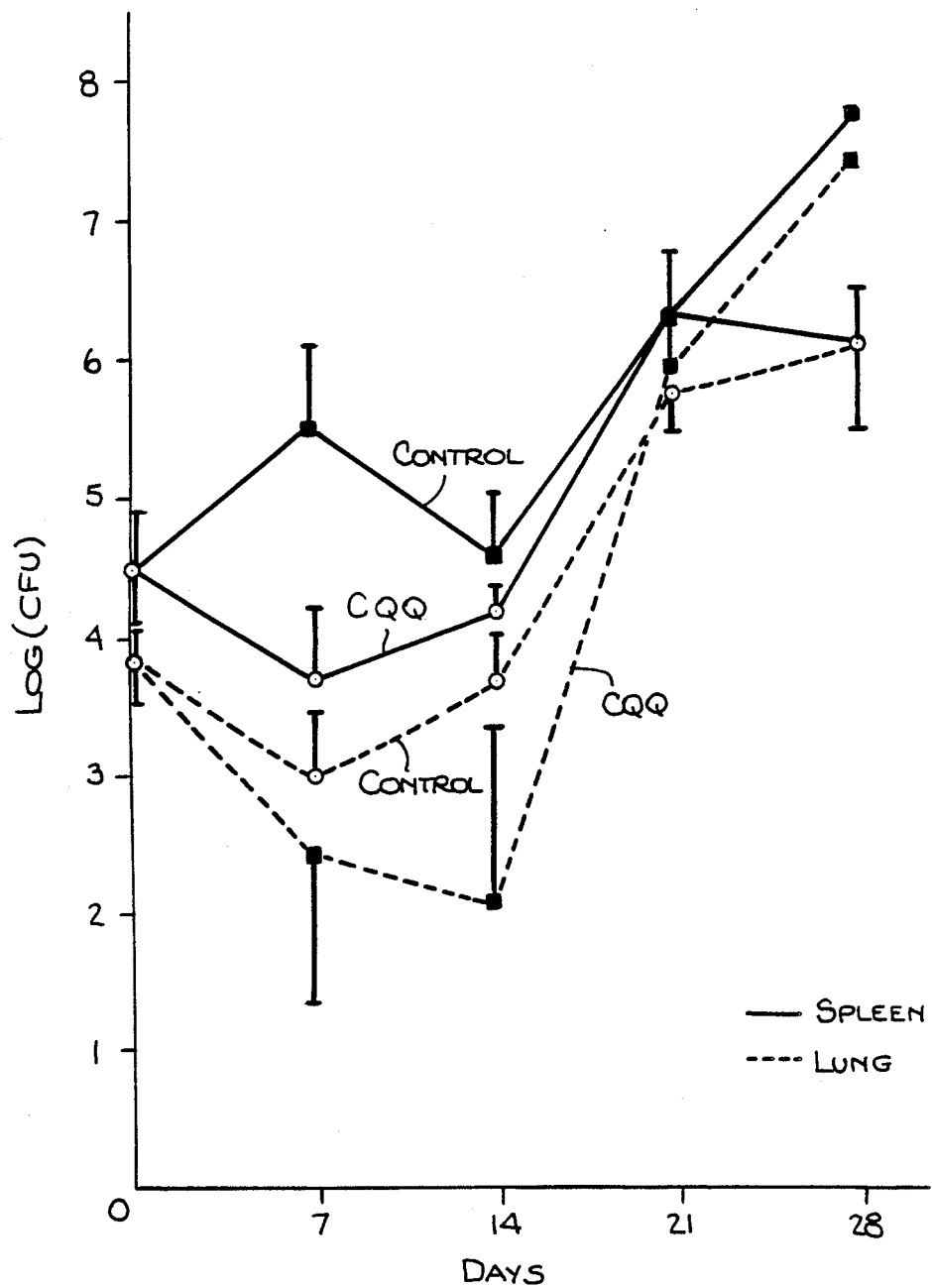

Essentially the same technique used in Experiment I was used, with CQQ given at 10 mg/kg daily orally and compared with an untreated infected control group. In this experiment, ansamycin was not used. CQQ again showed considerable antimycobactgerial activity with statistically significant differences in the CFU counts from spleen and lungs from the controls at 1,2 and 4 weeks (P 0.05) (FIG. 2).

EXAMPLE III
IN VIVO CHEMOTHERAPEUTIC ACTIVITY OF DIFFERENT DOSES OF GANGAMICIN AGAINST ACUTE M. INTRACELLULARE INFECTIONS IN BEIGE MICE

Figure 3:
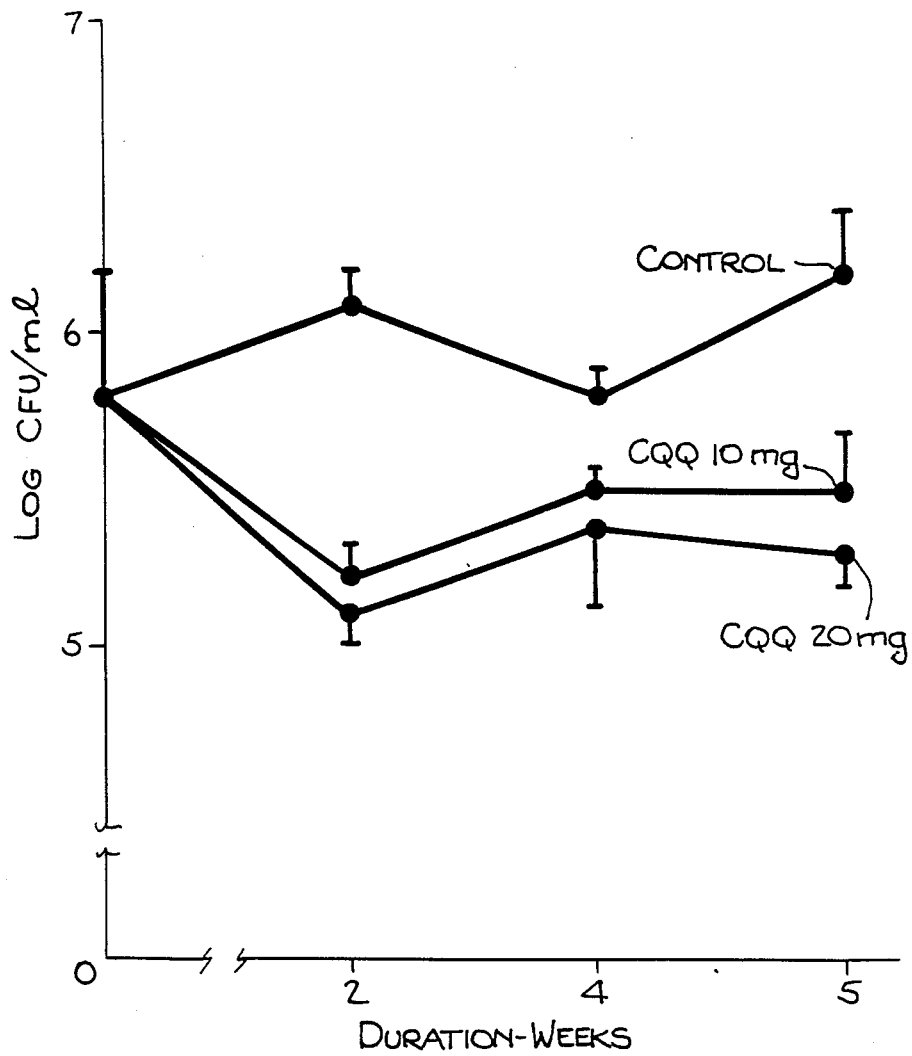
Figure 4:
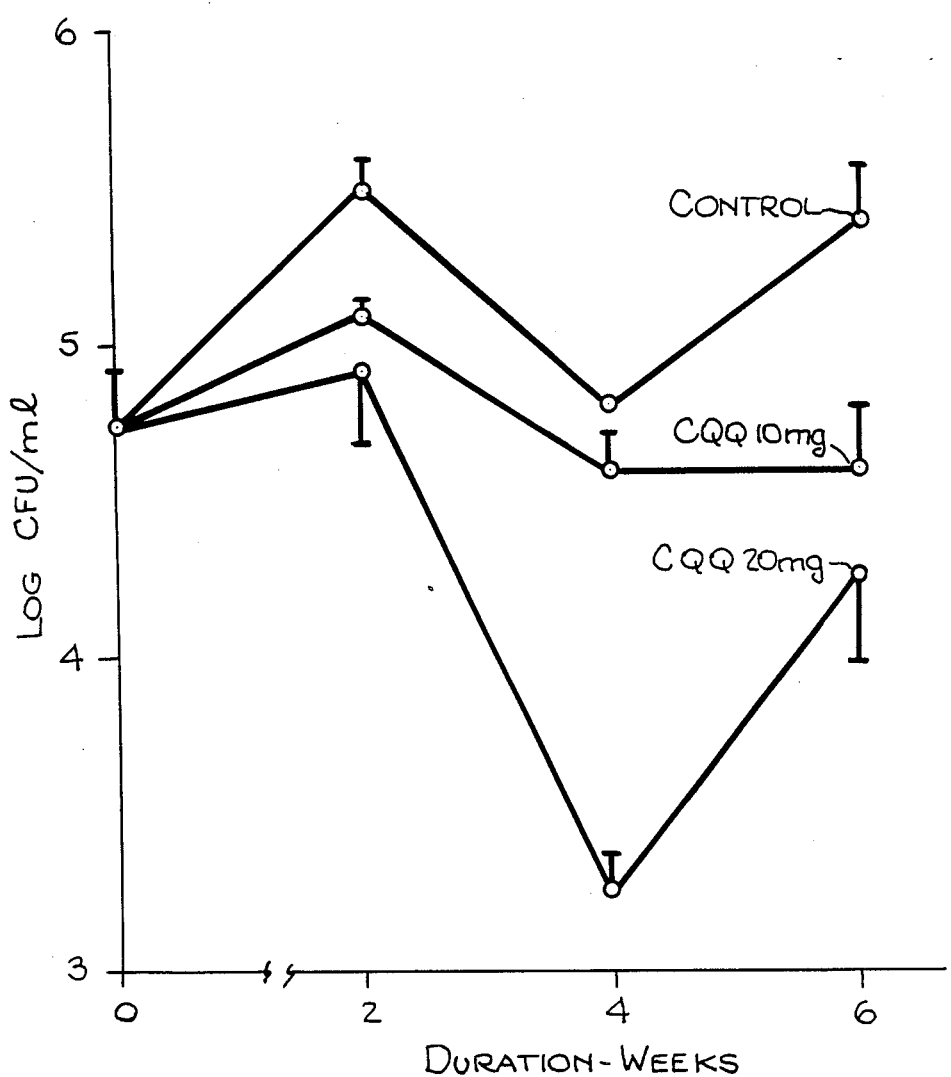

Beige mice infected intravenously with *M. intracellulare* (571-8 strain) were treated with CQQ at 10 or 20 mg/kg or none (control) and were followed as before. Again CQQ demonstrated considerable inhibitory activity as seen by the reduction of CFU counts from spleens (FIG. 3) and lungs (FIG. 4) with statistically significant differences up to 6 weeks (P 0.05). The dose of 20 mg/kg is better than 10 mg/kg dose and the effect of the drug is more pronounced in the lung (FIG. 4) than in the spleen (FIG. 3).

EXAMPLE IV
IN VIVO EFFECTIVENESS OF GANGAMICIN AGAINST CHRONIC M. INTRACELLULARE INFECTIONS IN C57BL/6 MICE

Figure 5:
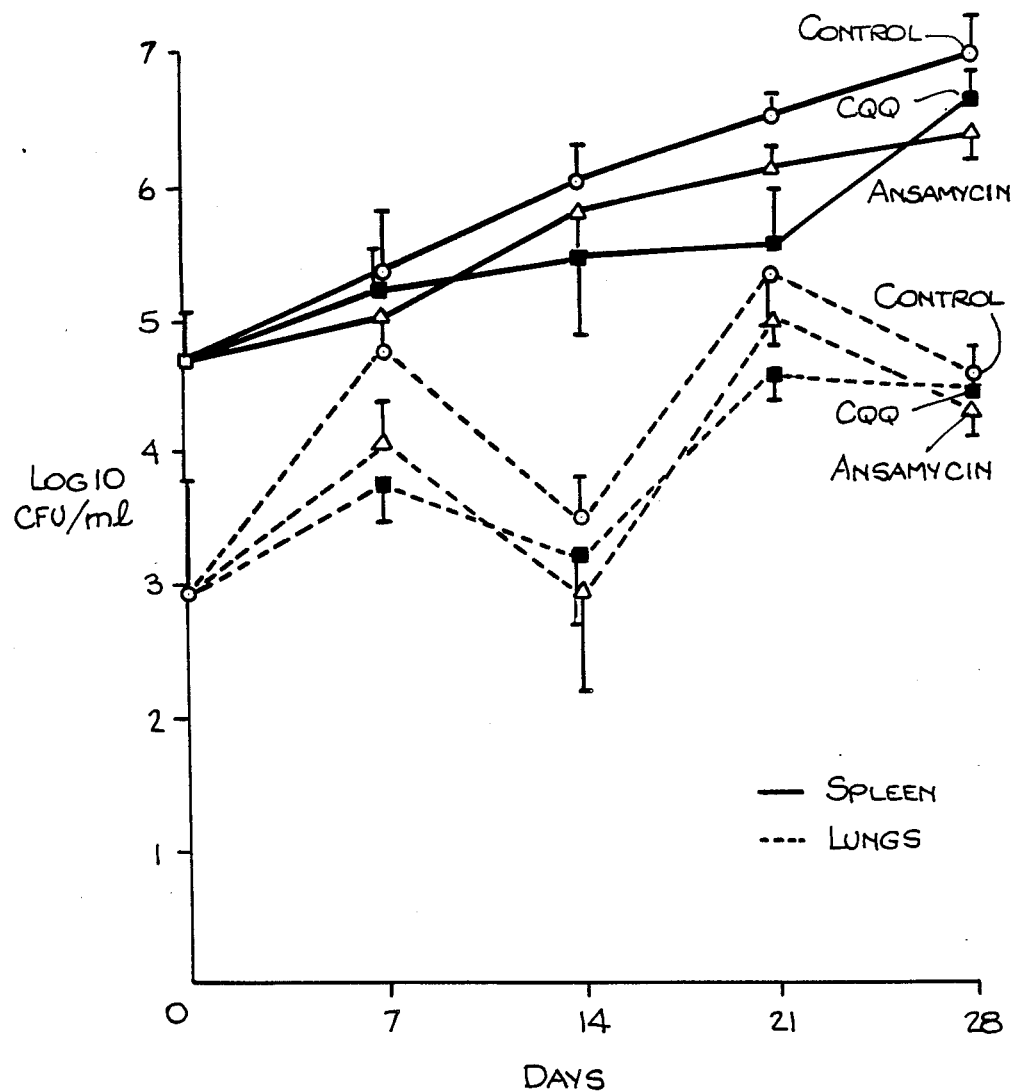

In this experiment, C57Bl/6 mice infected intravenously with *M. intracellulare* 571-8 strains were treated with either CQQ (10 mg/kg), Ansamycin (10 mg/kg) or none (control), and were followed for 28 days. At 1 day and weekly intervals, CFU counts of recoverable organisms from spleen and lungs were measured. CQQ at this dose showed considerable reduction in CFU counts both in spleen and lungs, as compared to untreated control (FIG. 5). The differences between the CQQ treated and control groups achieved statistical significance up to 3 weeks (P 0.05). Its activity is similar to that of ansamycin.

EXAMPLE V
IN VIVO CHEMOTHERAPEUTIC ACTIVITY OF CQQ AGAINST CHRONIC M. INTRACELLULARE INFECTIONS IN C57BL/6 MICE

Figure 6:
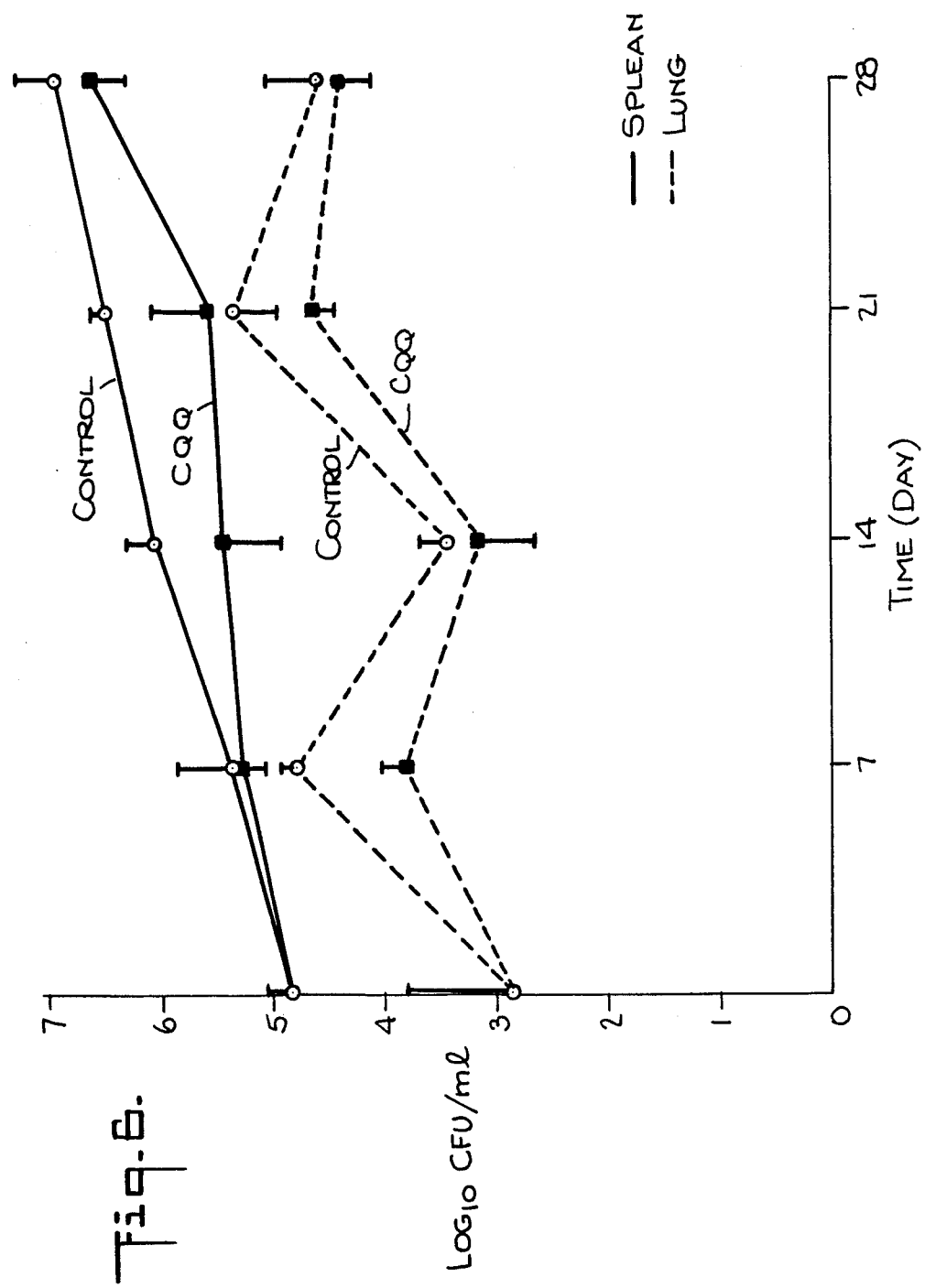

The same type of studies as in Example IV were repeated excepting ansamycin treatment were not included. Essentially similar results were obtained, showing considerable in vivo antimycobacterial activity of CQQ in the chronic infection (FIG. 6).

EXAMPLE VI
IN VITRO ACTIVITY OF GANGAMICIN AGAINST SEVERAL SEROVARS OF M. INTRACELLULARE

A study of the effect of CQQ on different serovars of *M. intracellulare* in vitro was performed using the radiometric (Bactec) method. Maximum growth index (GI) of 999 was determined (for control models) in terms of the number of days necessary for the culture to reach this stage. GI is measured using the special instrument which reads the amount of $^{14}C$ labelled $CO_2$ liberated from the strains using the $^{14}C$ labelled substrates.

Figure 7:
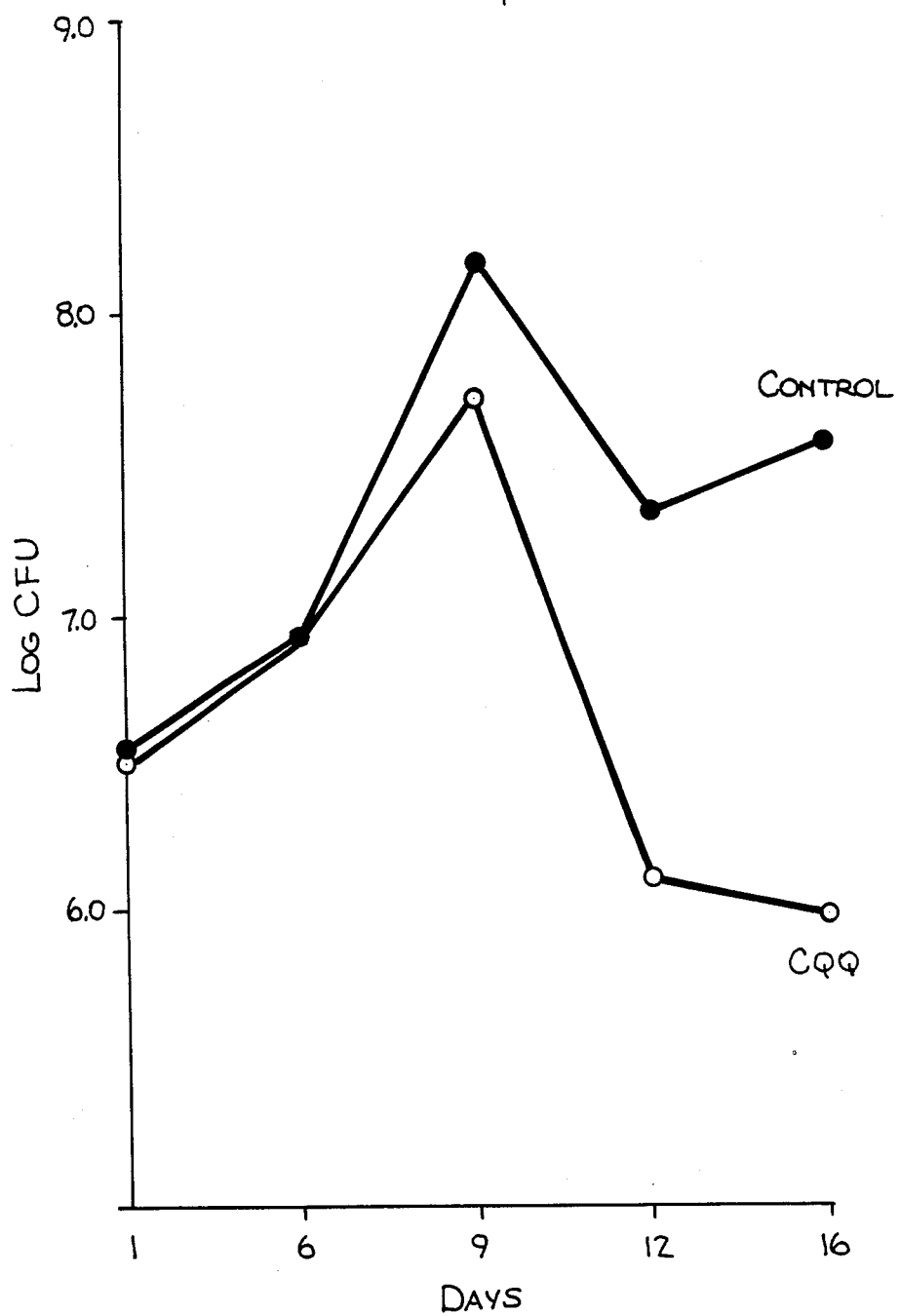

Table 1 shows the dramatic decrease in GI rates for all *M. intracellulare* strains at both concentrations of CQQ. Complete inhibition of the strains is event. In contrast, rifampin, a powerful antimycobacterial drug is only effective on a few strains.

mcg/ml while the other served as the untreated control. CQQ exhibited a remarkable inhibitory activity against tubercle bacilli (FIG. 7).

TABLE 1

CQQ SUSCEPTIBILITY STUDY
MAXIMUM GI AND DAY ACHIEVED
CONCENTRATION OF CQQ

| SEROVAR | STRAIN | 16.0 MCG/ML | | 8.0 MCG/ML | | CONTROL | |
|---|---|---|---|---|---|---|---|
| 4 | 7-55 | 4 | (2) | 7 | (2) | 999 | (4) |
|  | TMC1463 | 5 | (1) | 6 | (1) | 999 | (5) |
|  | 5-13 | 4 | (1) | 14 | (1) | 999 | (4) |
|  | 8-50 | 6 | (1) | 15 | (2) | 999 | (4) |
| 3 | 12-1 | 6 | (2) | 4 | (2) | 999 | (5) |
|  | 9-75 | 14 | (1) | 22 | (2) | 999 | (4) |
|  | 971-8 | 8 | (1) | 20 | (3) | 999 | (4) |
|  | 7-17 | 5 | (1) | 16 | (2) | 999 | (3) |
| 9 | 1784-286 | 5 | (1) | 9 | (1) | 999 | (6) |
|  | 2-10 | 12 | (1) | 14 | (1) | 999 | (5) |
|  | 7-25 | 7 | (1) | 33 | (4) | 999 | (4) |
|  | 6-38 | 6 | (1) | 13 | (1) | 999 | (4) |
| 14 | P-39 | 22 | (1) | 21 | (1) | 999 | (5) |
|  | 7-3 | 4 | (1) | 5 | (2) | 999 | (4) |
|  | 7-43 | 9 | (1) | 1 | (1) | 999 | (4) |
|  | BOONE | 7 | (1) | 13 | (1) | 999 | (3) |

EXAMPLE VII

IN VIVO ACTIVITY OF GANGAMICIN AGAINST M. TUBERCULOSIS INFECTIONS IN C57BL/6 MICE

In this experiment C57Bl/6 mice were infected intravenously with M. tuberculosis $H_{37}Rv$ strain and one group was treated daily orally with 10 mg/kg of CQQ and the others as untreated infected control. The mean CFU counts from spleens and lungs at the end of 4 weeks showed a considerable reduction in the CQQ treated as compared to the untreated controls (Table 2).

TABLE 2

| MEAN COLONY FORMING UNIT | SPLEEN | | LUNG | |
|---|---|---|---|---|
|  | CONTROL | CQQ | CONTROL | CQQ |
| (CFU) COUNT (LOG CFU) | 6.90 | 4.90 | 6.42 | 4.21 |

CQQ is thus clearly an effective antituberculosis agent.

EXAMPLE VIII

FURTHER IN VITRO STUDIES ON THE ACTIVITY OF GANGAMICIN AGAINST M. TUBERCULOSIS

In addition to the extensive in vitro studies done and reported, using M. intracellulare, experiments were done to assess the activity of CQQ at a concentration of 2 mcg/ml against growing culture of M. tuberculosis. Middlebrook 7H9 broth was inoculated with a young growing culture of M. tuberculosis $H_{37}Rv$ strain to a 1 week CQQ was added at a final concentration of 2

EXAMPLE IX

INHIBITORY ACTIVITY OF GANGAMICIN AGAINST MYCOBACTERIUM LEPRAE STUDIED IN THE MACROPHAGE MODEL

The effect of CQQ on Mycobacterium leprae, the causative agent for leprosy, was studied using monocyte derived macrophages obtained from human volunteers.

Blood from a healthy volunteer was drawn and monocytes were removed and cultured to the macrophage stage. This required about 7 days. The macrophages were then exposed to M. leprae bacilli obtained from biopsy specimens of leprosy patients. One sample was exposed to CQQ, while other samples were exposed to DDS (diaminodiphenyl sulphone), the standard antileprosy drug, or rifampin, at various concentrations. Macrophages were exposed to radiolabelled tritium ($^3H$) labeled thymidine, and its uptake was measured using a liquid scintillation counter. A control model of M. leprae exposed macrophages, which was not treated was used as well. The uptake of thymidine is a measure of antimycobacterial activity.

Table 3 presents the results of these experiments. CQQ in concentrations between 25 to 200 mg/ml showed significant inhibition of $^3H$ thymidine uptake in two strains of M. leprae. With another strain of M. leprae even greater activity was noted. Its activity in general is similar to that of DDS (10 mg/ml) and rifampin (3 mg/ml) under identical experimental conditions. These results show that CQQ demonstrates considerable antileprosy activity.

TABLE 3

| | | | | | COUNTS PER MINUTE | | | | | |
|---|---|---|---|---|---|---|---|---|---|---|
| | | | | | | CQQ | | | | |
| | AUTOCLAVE CONTROL | LIVE CONTROL | DDS (10 NG/ML) | RIF (3 NG/ML) | 200 NG/ML | 100 NG/ML | 50 NG/ML | 25 NG/ML | 10 NG/ML | 5 NG/ML |
| SAMPLE I | 1817 | 2812 | 84 | 82 | * | 84 | 93 | 93 | 2.3 | 2.4 |
| SAMPLE II | 1223 | 4171 | 78 | 80 | 91 | 76 | 76 | 69 | 13 | 6 |
| SAMPLE III | 515 | 394 | 84 | 82 | ND | ND | ND | 37 | 2 | 2 |

*CYTOTOXIC TO MACROPHAGES

EXAMPLE X

ACUTE AND CHRONIC TOXICITY OF GANGAMICIN

Studies were performed to obtain toxicity data. It has been determined that C57Bl/6 mice the $LD_{50}$ is 564 mg/kg, CQQ is administered intraperitoneally. Extrapolating, this corresponds to an $LD_{50}$ of approximately 40 gr for a 70 kg subject. For chronic toxicity studies both C57Bl/6 and Beige mice were administered doses of 40 mg/kg/day, and intraperitoneal doses over 30 mg/kg for more than 60 days. No visible toxic manifestation or death were noted in any of the animals during this period.

EXAMPLE XI

EFFECT OF GANGAMICIN ON BLOOD CLOTTING

Figure 8:
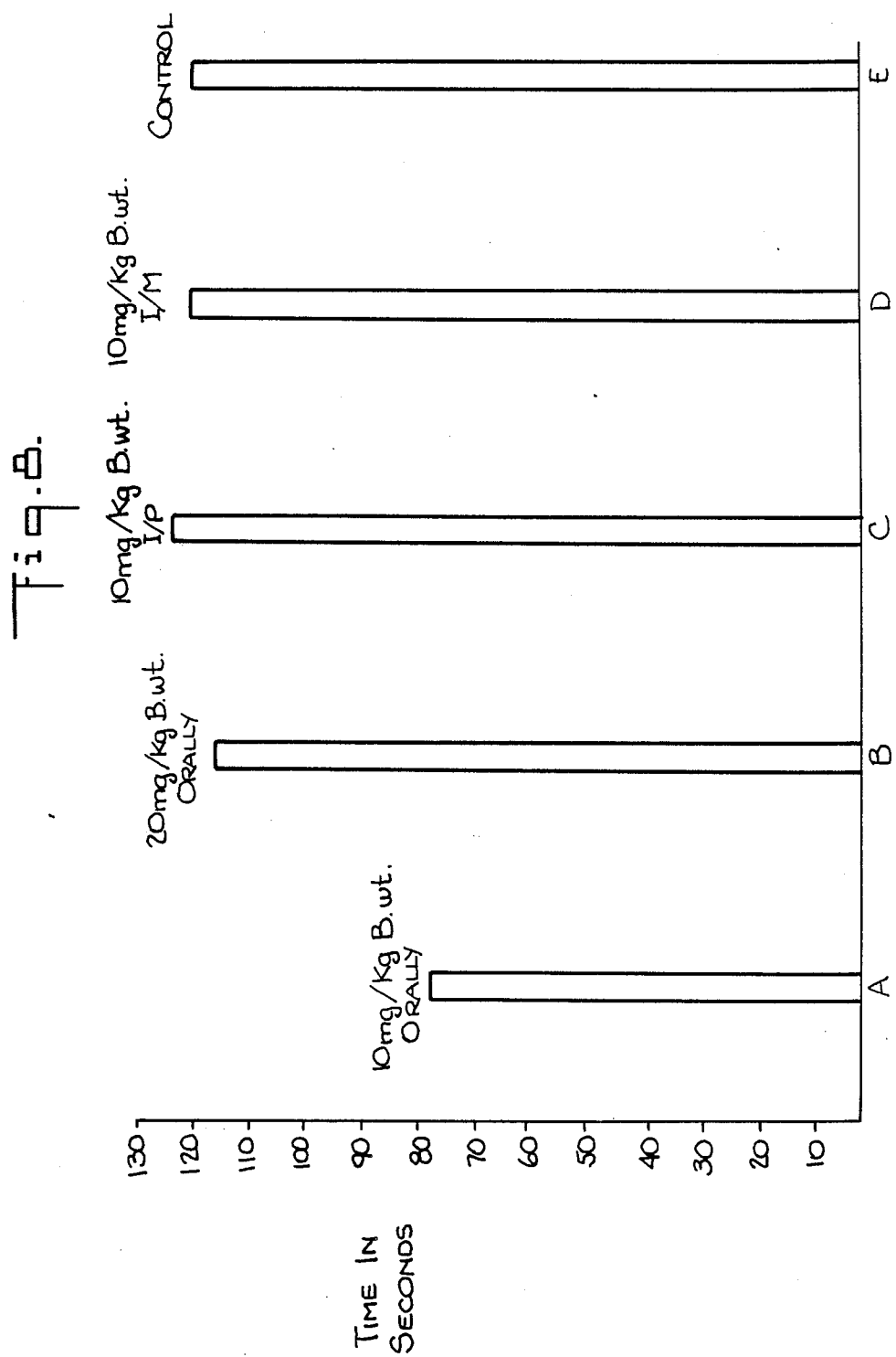

Due to its relationship to Vitamin K, there was some concern as to the effect CQQ would have on blood clotting. Varying amounts of CQQ were administered orally, intraperitoneally, and intramuscularly. As is shown in FIG. 8, there is little change in blood clotting time.

EXAMPLE XII

EFFECT OF GANGAMICIN ON CHROMOSOMAL STRUCTURES

In the study of any drug it is necessary to determine what effect, if any, the drug will have on chromosomes of the subject organism. This is especially important when the drug is intended for prolonged use.

In order to determine the effect of CQQ on chromosomes, blood was collected from a healthy male volunteer, and lymphocytes were isolated from the sample. These were cultivated in a folate deficient medium, and after approximately 24 hours of cultivation, 0.5 ml of a solution of CQQ (10 mcg/ml) was added to the culture. Incubation at 37° C. for 72 hours followed. The lymphocytes were then harvested, following routine laboratory porocedures and were stained with Giemsa stain. At least 50 cells were counted, and chromosomal breaks were observed in only 5 of these, and the number of breaks totalled 7. This is fully within the normal limits of compounds to be used as drugs.

EXAMPLE XIII

IN VITRO GROWTH INHIBITION OF MICROOCOCCUS LUTEUS BY GANGAMICIN

Figure 9:
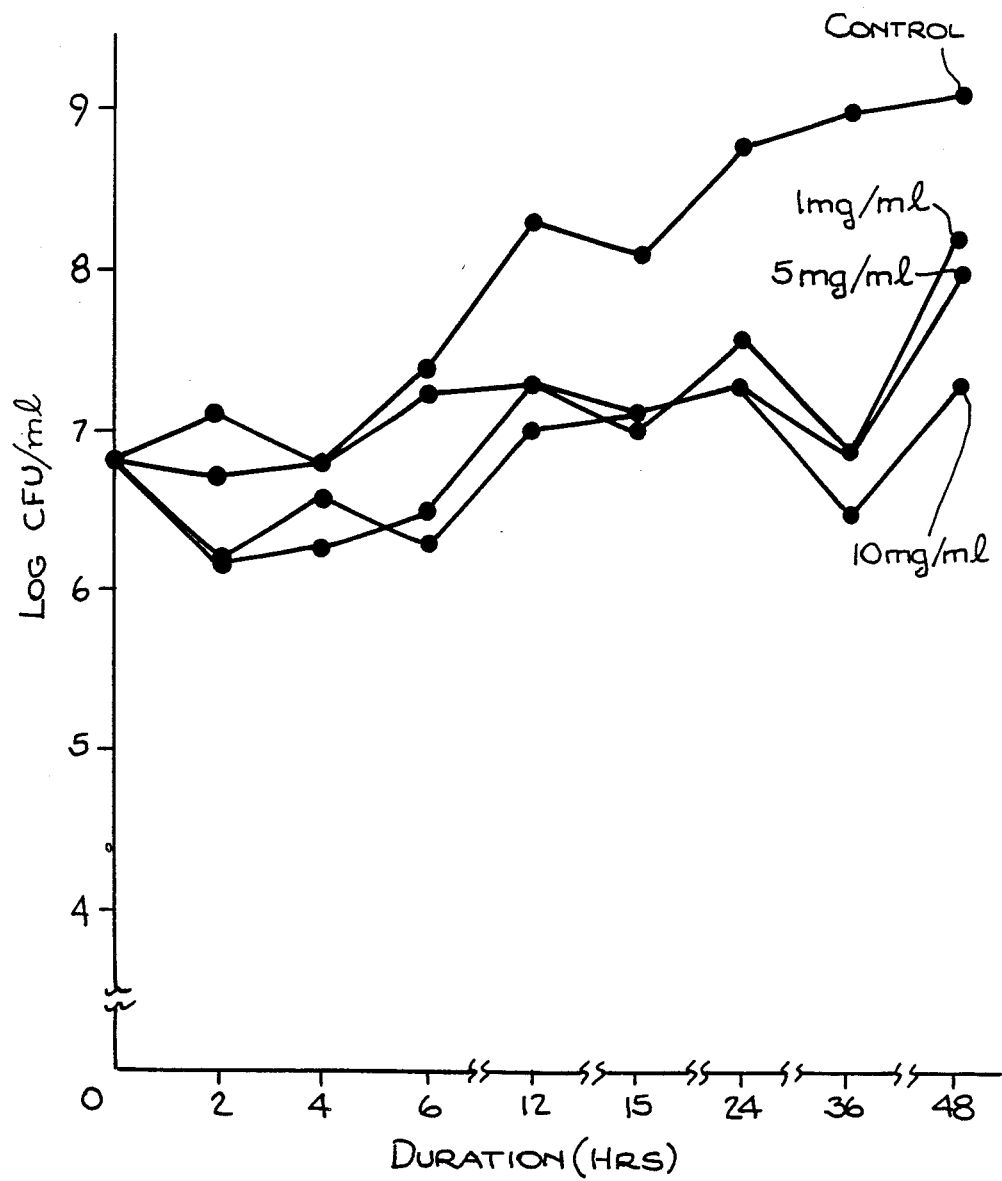

Studies were done to determine whether CQQ has a direct inhibitory activity on the organism *Micrococus luteus* in order to be able to develop a microbiological assay. Essentially, *Micrococcus luteus* was grown in nutrient broth, after which known concentrations of CQQ were added. The changes in the viable counts of the recoverable organisms on the tubes containing various concentrations of CQQ or no drug (control) were plated at various periods after initiation of the experiment. The counts were obtained by making ten-fold dilutions in saline and plating at 0.1 ml of the appropriate dilution onto the nutrient agar plate and spread with a turn-table to get a proper distribution of the inoculum onto the plate. After incubation for 48 hours at 37° C., the inoculated plates are read and colonies are visually counted. The number of colonies are converted into a logarmithic scale and plotted as shown in FIG. 9.

EXAMPLE XIV

ATTEMPTS TO DEVELOP A CHEMICAL ASSAY METHOD FOR GANGAMICIN

Figure 10:
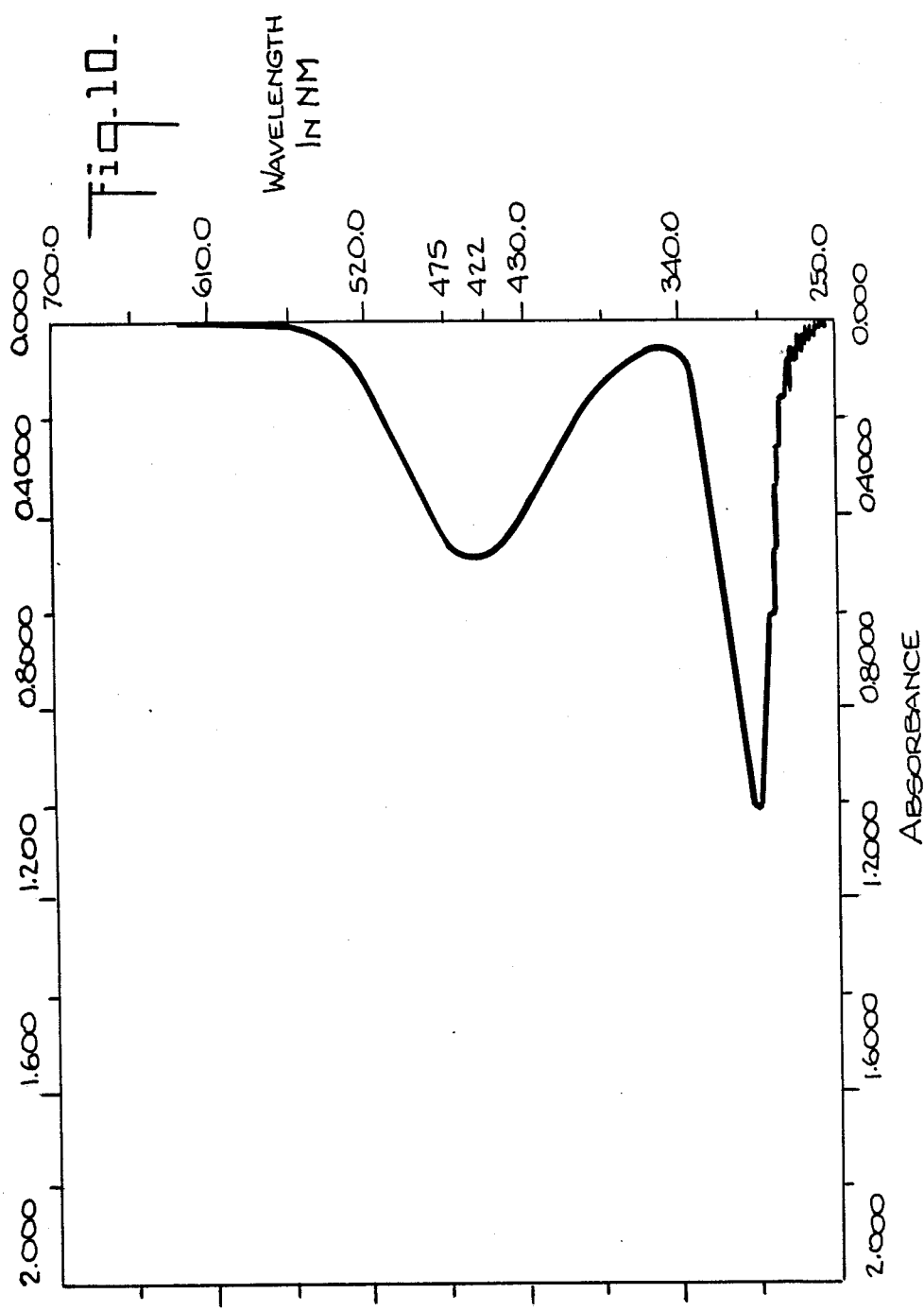

In order to develop a chemical method of estimation as well as study its structural chemistry, the absorption spectrum of CQQ was studied. CQQ was dissolved at a concentration of 10 mcg/ml in pure alcohol and readings taken with a scanning speed of 500 nm/minute using the spectrophotometer. The absorbance is plotted (FIG. 10) with respect to wavelength and 2 peaks one at 295 and 432 nm were noted. Subsequent studies involved the measurement of the absorbance of these two wavelength using varying concentrations of CQQ ranging from 10 to 100 mcg/ml in alcohol solution. Readings taken at 295 nm showed a standard relationship up to 0 to 40 mcg after which the absorbance rather stable. In other words, readings at 295 gave only reproducible assay method if the concentration involved is less than 40 mcg/ml. On the other hand, readings taken at 422 nm, showed leaner absorption from 0 to 100 mcg/ml concentration of CQQ (FIG. 10). It is possible to develop a chemical assay method of available levels of CQQ in tissues and blood, by taking readings of CQQ after extraction with suitable solvents, and taking the readings at one of these two wavelengths.

The experiments described supra clearly show the in vivo efficacy of CQQ in treating *M. tuberculosis* and *M. intracellulare* disease. Whether administered orally, intraperitoneally, subcutaneously, or in any other fashion familiar to one skilled in the art, the drug functions as an antimycobacterial and antileprosy agent, demonstrated activity against *M. tuberculosis*, *M. leprae* and more importantly against *M. intracellulare* against which no specific drugs are available. Its in vivo activity, as seen in immunesuppressed Beige mice, which are similar to AIDS patients, warrants special consideration of its potential value.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A method of treating tuberculosis in mammals comprising administering to an individual infected with tuberculosis causing bacteria an effective amount of 6-cyclo-octylamino-5,8-quinoline quinone sufficient to inhibit said tuberculosis causing bacteria and infections arising therefrom.

2. A method as in claim 1, wherein said infection is caused by *M. tuberculosis* bacteria.

3. A method as in claim 1, wherein said infection is caused by *M. intracellulare* bacteria.

4. A method as in claim 1, wherein said compound is administered in an amount ranging up to about 600 mg/kg of body weight.

5. A method as in claim 1, wherein said compound is administered in connection with a pharmaceutically acceptable non-toxic carrier.

6. A method as in claim 1, wherein said compound is administered in an amount ranging up to about 60 mg/kg of body weight on a daily basis.

7. A method as in claim 1, wherein said compound is administered orally.

8. A method as in claim 1, wherein said compound is administered parenterally.

9. A method as in claim 1, wherein said compound is administered intravenously.

10. A method as in claim 1, wherein said compound is administered intramuscularly.

11. A method of treating leprosy in mammals comprising administering to an individual infected with Mycobacterium leprae bacteria an amount of 6-cyclooctylamino-5,8-quinoline quinone sufficient to inhibit said bacteria and infections arising therefrom.

12. A method as in claim 11, wherein said 6-cyclooctylamino-5,8-quinoline quinone is administered in a concentration from about 5 mg/ml to no more than 200 ng/ml.

* * * * *